United States Patent [19]
Zarchan

[11] Patent Number: 6,075,755
[45] Date of Patent: Jun. 13, 2000

[54] MEDICAL REMINDER SYSTEM AND MESSAGING WATCH

[75] Inventor: David Zarchan, Concord, Mass.

[73] Assignee: Recall Services, Inc., Concord, Mass.

[21] Appl. No.: 09/013,082

[22] Filed: Jan. 26, 1998

Related U.S. Application Data

[60] Provisional application No. 60/046,187, May 12, 1997.

[51] Int. Cl.[7] .............................. G04B 47/00; G07F 11/00
[52] U.S. Cl. .................................................. 368/10; 221/3
[58] Field of Search .............................. 368/10, 107–109; 221/2, 3, 15; 340/309.15, 309.4; 364/413.02, 569

[56] References Cited

U.S. PATENT DOCUMENTS

| | | |
|---|---|---|
| 3,739,740 | 6/1973 | Fromer . |
| 3,762,601 | 10/1973 | McLaughlin . |
| 3,917,045 | 11/1975 | Williams et al. . |
| 4,057,145 | 11/1977 | Wray et al. . |
| 4,063,410 | 12/1977 | Welling . |
| 4,223,801 | 9/1980 | Carlson . |
| 4,258,354 | 3/1981 | Carmon et al. . |
| 4,266,102 | 5/1981 | Stanley et al. . |
| 4,275,384 | 6/1981 | Hicks et al. . |
| 4,293,845 | 10/1981 | Villa-Real . |
| 4,302,752 | 11/1981 | Weitzler . |
| 4,360,125 | 11/1982 | Martindale et al. . |
| 4,361,408 | 11/1982 | Wirtschafter . |
| 4,419,016 | 12/1983 | Zoltan . |
| 4,504,153 | 3/1985 | Schoiimeyer et al. . |
| 4,588,303 | 5/1986 | Wirtschafter et al. . |
| 4,616,316 | 10/1986 | Hanpeter et al. . |
| 4,617,557 | 10/1986 | Gordon . |
| 4,674,652 | 6/1987 | Aten et al. . |
| 4,682,299 | 7/1987 | McIntosh et al. . |
| 4,712,562 | 12/1987 | Ohayon et al. . |
| 4,731,765 | 3/1988 | Cole et al. . |
| 4,748,600 | 5/1988 | Urquhart ................................... 368/10 |
| 4,766,542 | 8/1988 | Pilarczyk . |
| 4,768,176 | 8/1988 | Kehr et al. . |
| 4,768,177 | 8/1988 | Kehr et al. . |
| 4,803,625 | 2/1989 | Fu et al. . |
| 4,837,719 | 6/1989 | McIntosh et al. . |
| 4,942,544 | 7/1990 | McIntosh et al. . |
| 4,970,669 | 11/1990 | McIntosh et al. . |
| 5,011,032 | 4/1991 | Rollman . |
| 5,088,056 | 2/1992 | McIntosh et al. . |
| 5,097,429 | 3/1992 | Wood et al. . |
| 5,099,463 | 3/1992 | Lloyd et al. . |
| 5,157,640 | 10/1992 | Backner . |
| 5,159,581 | 10/1992 | Agans . |
| 5,200,891 | 4/1993 | Kehr et al. . |
| 5,400,301 | 3/1995 | Rackley . |
| 5,408,443 | 4/1995 | Weinberger ................................ 368/10 |
| 5,412,372 | 5/1995 | Parkhurst et al. . |
| 5,495,961 | 3/1996 | Maestre ..................................... 368/10 |
| 5,547,878 | 8/1996 | Kell . |
| 5,554,967 | 9/1996 | Cook et al. . |
| 5,577,335 | 11/1996 | Tucker . |
| 5,582,323 | 12/1996 | Kurtenbach . |
| 5,646,912 | 7/1997 | Cousin ...................................... 368/10 |

*Primary Examiner*—Vit Miska
*Attorney, Agent, or Firm*—Charles G. Call

[57] ABSTRACT

A Medical Reminder System has an electronic messaging watch which is programmed with a medication regimen for the patient via an infrared or other electronic data transfer link to a health care provider's computer system having custom software. The programmable watch sounds an alarm when a medication is to be taken, or a health care procedure is to be performed. Each watch is programmed with the patient's name, individual medicine names, dosage amounts and specified medication times, as well as with alerts for appointments, prescription refills and medical events. Non-medical messages may also be programmed into the watch. The alarm consists of distinctive monotone beeps and is sounded by the watch at the preset times programmed by the health care provider. The medication information scrolls across the screen when the patient records the event by pressing a button on the watch. The watch is programmed by placing it into a custom cradle that facilitates information transfer between the computer and the watch by means of infrared or other electronic signals. The watch monitors and graphically shows which medications have been taken on a daily basis, as well as allowing the patient to record "medical events" into the watch's memory, allowing the level of compliance and patient history to be reviewed.

8 Claims, 15 Drawing Sheets

CAPOTEN 25MG / LASIX 40MG / LANOXIN .125MG ● CAPOTEN 25
Fig. 8
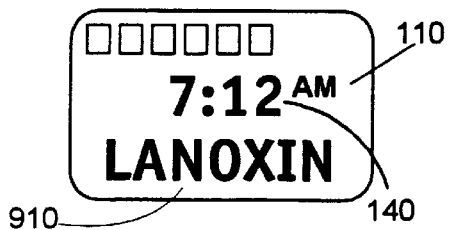
Fig. 9
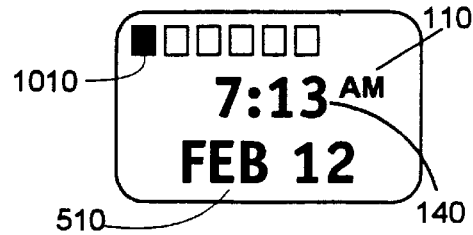
Fig. 10
EARLY? TO TAKE MEDS EARLY, PRESS MED BUTTON AGAIN; OTHERWISE PRESS ANY OTHER BUTTON
Fig. 11
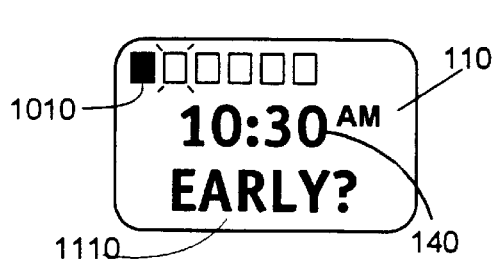
Fig. 12
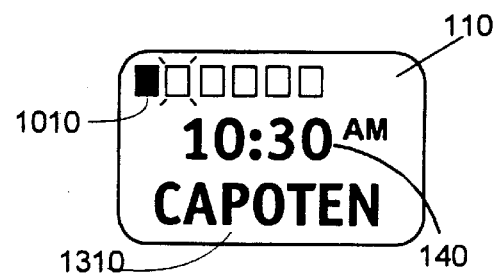
Fig. 13
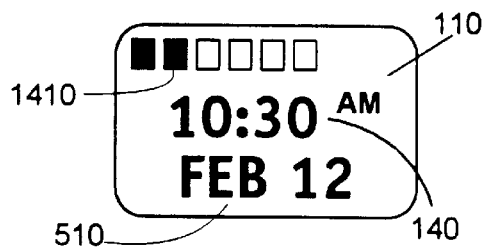
Fig. 14
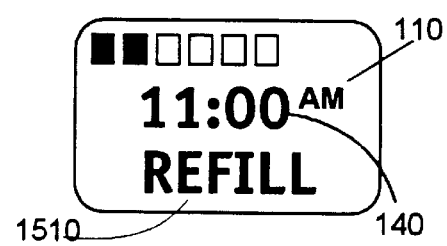
Fig. 15

RETURN TO PHARMACY FOR CAPOTEN REFILL
APPOINTMENT WITH DR. EDWARDS MARCH 14 AT 2:00 PM
Fig. 16
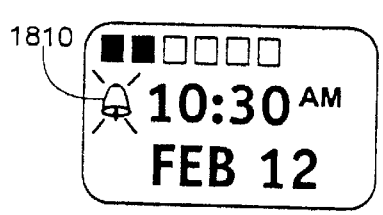
Fig. 17
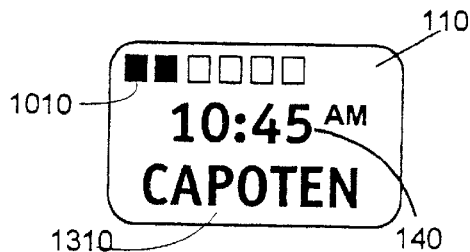
Fig. 18
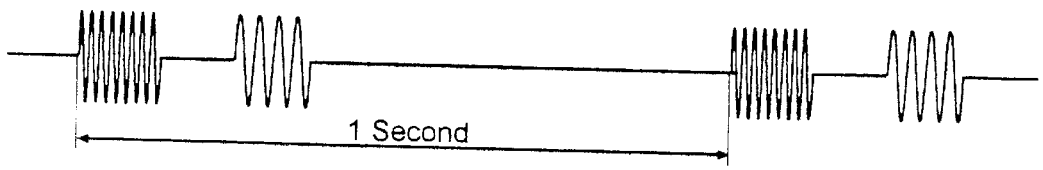
Fig. 19
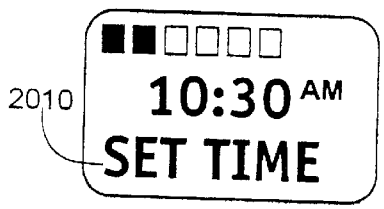
Fig. 20
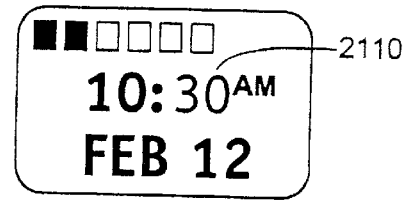
Fig. 21
Fig. 22
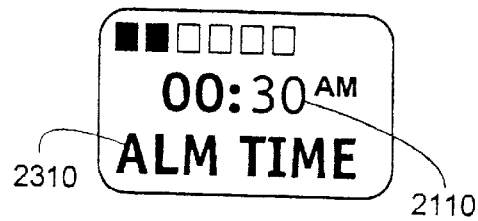
Fig. 23

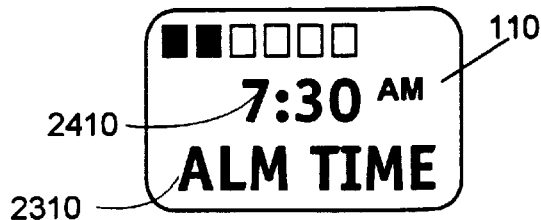
Fig. 24
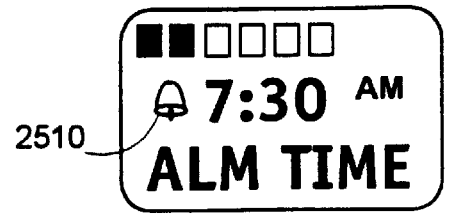
Fig. 25
Fig. 26
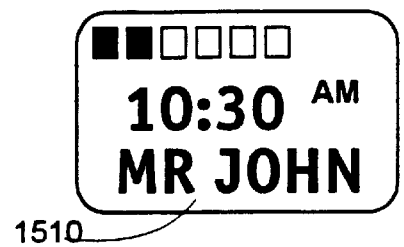
Fig. 27
MR JOHN R. SMITH. (800) 123-4567
Fig. 28
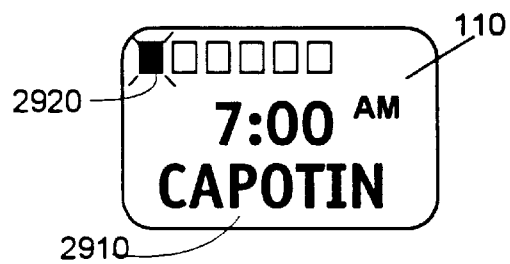
Fig. 29

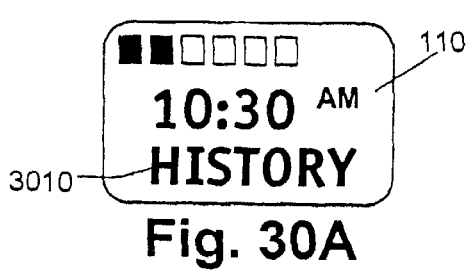
Fig. 30A
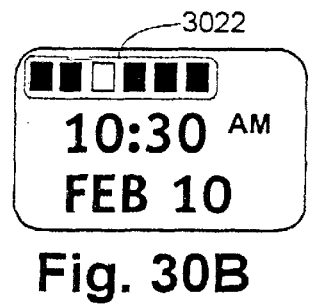
Fig. 30B
125/140 = 89% SUCCESS
Fig. 31
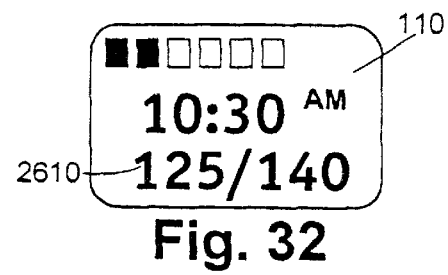
Fig. 32
Fig. 33A
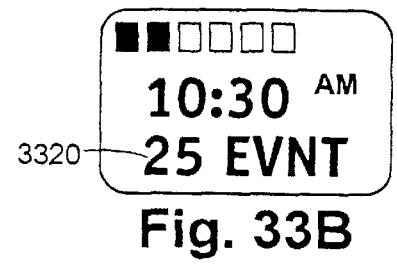
Fig. 33B
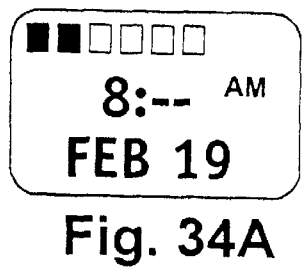
Fig. 34A
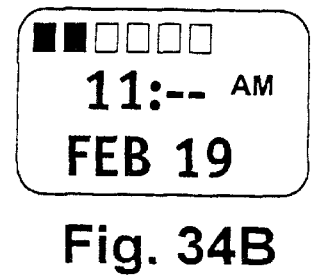
Fig. 34B
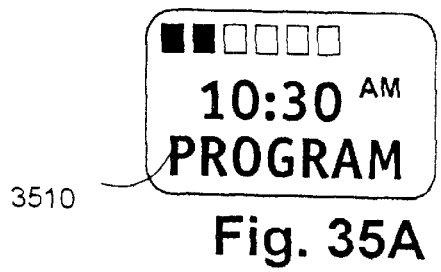
Fig. 35A
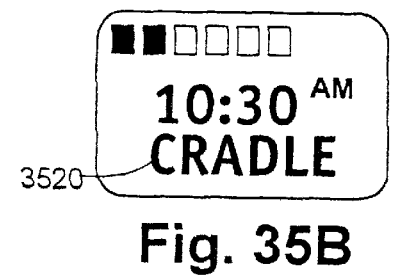
Fig. 35B Elevated Cholesterol - Congestive Heart Failure 7:00 AM Capoten 25mg/Lasix 40mg/Lanoxin 125mg
3:00 PM Capoten 25mg/Lasix 40mg
10:00 PM Capoten 25mg/Pravachol 20mg Hypertension 7:00 AM Hydrochlorthlazide 25mng/Atenolol 50mg/Zestril 10mg
7:00 PM Zestril 10mg Epilepsy 7:00 AM Dilantin 100mg/Mysoline 250mg
3:00 PM Dilantin 100mg/Mysoline 250mg
10:00 PM Dilantin 100mg/Mysoline 250mg/Phenobarbitol 60mg Diabetes 6:00 AM NPH Insulin 30 Units/Regular Insulin 4 Units
2:00 PM Regular Insulin 8 Units Severe Asthma 7:00 AM Proventil Inhaler2/Beclovant Inhaler2/Sio-bid 200mg/Prednisona 10 mg
12:00 PM Proventil Inhaler2/Beclovant Inhaler2
6:00 PM Proventil Inhaler2/Beclovant Inhaler2
7:00 PM Sio-bid 200mg
11:00 PM Proventil Inhaler2/Beclovant Inhaler2

Fig. 39
Fig. 40

Patient Name: Duckworth, Jim          Program Issue Date: 2/26/97
Patient ID:   111-11-111
Telephone:    555-1212

Date   Time    Watch Message

Medication Reminders:
    7:00 AM CAPOTEN 25 MG / LASIX 40 MG / LANOXIN .125 MG
    3:00 PM CAPOTEN 25 MG / LASIX 40 MG
    10:00 PM CAPOTEN 25 MG / PRAVOCHOL 20 MG Home Health Test Reminders:
    3:00 PM MONITOR BLOOD PRESSURE..

Appointments:
2/8/97          APPOINTMENT WITH DR. EDWARDS ON FEB. 8 AT 1:00 PM.

Refills:
4/1/97          RETURN TO PHARMACY FOR CAPOTEN REFILL
4/1/97          REFILL LASIX AT PHARMACY
4/1/97          REFILL LANOXIN AT PHARMACY
4/15/97         REFILL PRAVACHOL AT PHARMACY Comments:

Disclosure and Disclaimer:
The ReCall program is intended to assist participants in adhering to their own set schedule of medications, home testing, and medical appointments. The ReCall program is only a supplement to any log, checklist, or memory system that the participant has established. The participant maintains full responsibility to administer all medications or home tests at their appropriate times. The ReCall program does not make any guarantees of reliability or any other warranty whatsoever.

I have read, fully understand, and agree to the Disclosure and Disclaimer section that appears above.

Patient Signature: _____ Date:_____ Clinician
Signature:_____ Date:_____

Fig. 43

MEDICAL REMINDER SYSTEM AND MESSAGING WATCH

CROSS REFERENCE TO RELATED APPLICATION

This application claims priority from provisional application number 60/046,187 filed on May 12, 1997.

FIELD OF THE INVENTION

The present invention relates to medical reminder systems and, in particular, to a system for providing programmable electronic auditory and/or visual reminders for medications and health care procedures.

BACKGROUND

Remembering to accurately take medication is well understood to be a very serious health problem, particularly for the elderly, for whom the taking of multiple medications is common. Often the appropriate efficacy levels of the medication are not reached or maintained, resulting in deterioration of health status and increased need of preventable hospital days and medical procedures. Noncompliance, defined in medical parlance as the failure to follow through with therapy as prescribed by one's physician, is recognized as a major impediment to improved health.

More than 80% of the 36.3 million people over 65 are on an active medication regimen, typically taking multiple medications daily. It is estimated that approximately fifty percent (50%) of patients with illness do not comply with their medication regimen, with the elderly making up a significant portion of this population. Failure to comply with one's medication regimen is associated with deterioration of health status, resulting in an escalation of medical costs for individuals and insurers, as well as an increase in preventable fatalities. The annual cost of noncompliance is estimated to exceed $100 billion.

A significant portion of compliance problems result from patients' difficulty in remembering to properly follow complicated treatment (i.e. multiple medications). The drop off rate for refilling medications for chronic diseases is very high, with up to 75% of monthly prescriptions not refilled after one (1) year. Forgetfulness to self-administer the prescribed medications at the correct daily intervals and correct dosages by patients has long been found to be a major impediment for doctors in determining the effectiveness of prescriptions. It is also well know that the more frequently a medication must be taken, the less likely the patient's compliance. Pharmaceutical companies consequently spend tremendous sums of money and time developing medications that need be taken only once daily, but many medications are simply not amenable to once-daily dosing regimes.

For the patient who must take three, four, or even five dosages of several medications daily, the prescribed regimens can easily become confusing. Many patients carry written timetables with them during the day. Pills are often set up in adjustable packets which can "line up" the medications to be taken. This can be effective, but does not solve the possibility of the patient becoming distracted or simply forgetful.

Some electronic reminder systems do exist, such as that described in U.S. Pat. No. 5,157,640 to Backner (1992). The Backner system utilizes a programmable electronic watch that generates different tones to indicate the number of types of medications to be taken and identifies the medication and dosage in a limited display on the face of the watch. The watch is programmed via connecting pins in a cradle linked to the programming computer. One problem with this approach is that the connecting pins frequently become dirty or damaged, causing the transfer to fail. Metal pins can also cause susceptibility of the system to Electro-Static Discharge (ESD). The Backner system also only allows limited identification information to be transferred from the watch to the host computer and thus does not provide for full two-way information transfer both to and from the watch in order to allow downloading of compliance and patient medical event information to the host computer for review by the physician, pharmacist, or other health care provider.

What is needed, therefore, is a device that can improve and monitor compliance with medication regimens. Such a device should provide automatic auditory and/or visual reminders for both daily medications and health care procedures, and should be programmable by a physician, pharmacist, or other health care provider in an efficient and convenient manner. In addition, such a device should allow two-way information transfer, allowing the patient to enter information into the watch, in order that the patient's compliance and other health events can be monitored by the health care provider.

OBJECTS OF THE INVENTION

Accordingly, a primary object of the present invention is to provide programmable electronic auditory and visual reminders for daily medication and health care procedures.

In particular, an object of the present invention is to provide a two-way watch to computing device transmission system that allows the watch to be programmed by sending data and commands from the personal computer and allows the user to enter specific responses into the watch for transfer to the computing device.

A further particular object of this invention is to conveniently and efficiently transfer data between an external data source or data utilization device and a watch or other small electronic device.

An additional particular object of this invention is to provide an electronic watch capable of providing medication and health care procedure reminders and tracking patient compliance and health events, as well as providing normal watch functions.

SUMMARY OF THE INVENTION

The Medical Reminder System of the invention provides a patient with programmable electronic auditory, vibratory and/or visual reminders for medications to be taken and health care tests or procedures to be performed at specific times of the day. The device used for this display also doubles as a normal electronic LCD watch. The medication schedule, along with other information such as appointment and refill reminders or home health tests or procedures to be performed, is downloaded to the watch device via an infrared or electronic link from the host PC containing the patient information.

The host system is comprised of a computer with custom software which can be incorporated into the health care provider's own patient medication tracking system. Each patient has an individual record which contains the patient's name, medical history, medication regimen, prescription history, and scheduled medical tests to be performed. Instructions for multiple times for medication or home health test or procedure reminders can be programmed into the watch. The watch therefore is also a data collection device, and can be programmed from the host computer system either through a modem or a dedicated docking cradle having the ability to upload and download data through infrared detectors and transmitters or other data communications electronics. This data collection device has the further ability to generate custom reports of collected information gathered by the device via the administrative software programs.

The watch functions as a normal watch until the medication alarm is sounded, at which point the watch display flashes the word "MEDICINE". The patient acknowledges the alarm by pressing the "MED" button, one of four buttons present on the side of the watch. The names and dosage quantity of the medications to be taken at this time are displayed across the lower portion of the LCD. Multiple alarms can be programmed into the watch for the same time, with each alert's medication information being unique.

The watch face has rectangular graphic outline boxes at the top of the LCD. The number of boxes correspond to the number of times medications or home health tests should be administered. These boxes are filled when the patient presses the MED button when the alarm is sounding, and provide a visual record to the patient for tracking the daily scheduled medicine regimen. The alarm will sound for a maximum of 30 seconds and will shut itself off if the patient presses the med button. The word "MEDICINE" continues to flash across the watch face for 59 minutes or until the MED button is pushed, while the audio alarm will continue to repeat every 10 minutes during that 59 minutes. The patient has up until the end of that 59 minutes to acknowledge the message and take the prescribed medication in order to comply with the medicine regimen, after which time the system records noncompliance.

The information that scrolls across the LCD is typically customized for each patient by the pharmacist or health care provider; the patient cannot alter that information by reprogramming of the watch. Programming can only be done when the watch is linked to the host computer. Any custom message can be programmed into the watch by the pharmacist or other health care provider.

A refill reminder can be programmed into the watch. The word "REFILL" appears across the LCD after the medication reminder alarm has sounded and the patient has pressed the med button twice. The patient then presses the med button again and the message about which medication(s) to refill scrolls across the watch screen. This refill reminder is set to alert the patient several days before the medication runs out.

The watch has a feature that allows the patient to take the prescribed medication at a time earlier than programmed, allowing the patient to keep to a prescribed regimen but still plan ahead so that the alarm does not sound at an inappropriate time. Appointments can also be programmed into the watch. The word "APPTMNT" appears across the LCD after the alarm has sounded and the patient has pressed the med button. The appointment message scrolls across the watch screen after the medicine regimen is displayed. This appointment reminder is set to alert the patient he has an appointment scheduled in the future. In a preferred embodiment, the watch additionally has a history mode that can be accessed by pressing the MODE button until the HISTORY word is displayed, providing the patient with a visual record of his or her compliance success rate.

The watch has a feature for recording medical events. The patient records the medical event by pressing the EVENT button on the side of the watch. The watch records the action and date stamps the event record. This medical event record can be retrieved by either the patient or the doctor by pressing the MODE button.

The watch has the ability to upload the data stored in the watch to the pharmacist or managed care provider's host computer. The Administrative Program that is located on the host computer can produce detailed formatted reports from the data that is uploaded to the computer from the watch, including graphic records of compliance In one embodiment of the system, the watch is designed to be programmed and used as a system to lead the patient through a series of questions and then collect the patient's responses. Specific questions and response options are programmed through administrative software. The watch may also prompt the patient for specific information at set times of the day, or to respond to other questions by selecting from a set of alternative choices. This embodiment of the watch allows multiple events to be recorded. The name and description of events that may be recorded may be programmed into the watch on a patient-by-patient basis using the Administrative software.

BRIEF DESCRIPTION OF THE DRAWINGS

FIG. 8 is a diagram showing the scrolling medication information displayed on the watch of FIG. 6 after the MED button has been pressed;

FIG. 9 is a diagram of the display of the watch of FIG. 6 after the MED button has been pressed;

FIG. 10 is a diagram of the display of the watch of FIG. 6 after the medication has been taken and the MED button pressed again;

FIG. 11 is a diagram showing the scrolling information displayed on the watch of FIG. 1 in the "advance operation" mode;

FIG. 12 is a diagram of the display of the watch of FIG. 1 in the "advance operation" mode;

FIG. 13 is a diagram of the display of the watch of FIG. 12 in the "advance operation" mode after the MED button has been pressed a second time, displaying the medication to be taken;

FIG. 14 is a diagram of the display of the watch of FIG. 12 when returned to "normal operation" mode;

FIG. 15 is a diagram of the display of the watch of FIG. 1 in the "refill reminder" mode;

FIG. 16 is a diagram showing the scrolling information displayed on the watch of FIG. 15 in the "refill reminder" mode;

FIG. 17 is a diagram of the display of the watch of FIG. 15 returned to the "normal operation" mode but showing the refill icon;

FIG. 18 is a diagram of the display of the watch of FIG. 1 in the "daily alarm" mode, FIG. 19 is a timing diagram of the daily alarm beep of the watch of FIG. 18 in the "daily alarm" mode;

FIG. 20 is a diagram of the display of the watch of FIG. 1 in the user-initiated "set time" mode;

FIG. 21 is a diagram of the display of the watch of FIG. 20 in the "set minutes" mode, showing the flashing minutes display;

FIG. 22 is a diagram of the display of the watch of FIG. 1 in the user-initiated "set alarm" mode;

FIG. 23 is a diagram of the display of the watch of FIG. 22 in the "set alarm" mode, showing the flashing minutes display;

FIG. 24 is a diagram of the display of the watch of FIG. 23, showing the newly set alarm time;

FIG. 25 is a diagram of the display of the watch of FIG. 24, showing the alarm icon;

FIG. 26 is a diagram of the display of the watch of FIG. 1 in the user-initiated "review medication schedule" mode;

FIG. 27 is a diagram of the display of the watch of FIG. 26 showing the patient information display;

FIG. 28 is a diagram showing the scrolling information displayed on the watch of FIG. 27;

FIG. 29 is a diagram of the display of the watch of FIG. 26 in the user-initiated "review medication schedule" mode, showing the medication description;

FIGS. 30A and B are diagrams of the display of the watch of FIG. 1 in the user-initiated "review history" mode;

FIG. 31 is a diagram showing the scrolling compliance information displayed on the watch of FIG. 30;

FIG. 32 is a diagram of the display of the watch of FIG. 30 showing the compliance ratio;

FIGS. 33A and B are diagrams of the display of the watch of FIG. 1 in the user-initiated "review events" mode;

FIG. 34A and B are diagrams of the display of the watch of FIGS. 33 A and B showing the events recorded on a particular date;

FIGS. 35A and B are diagrams of the display of the watch of FIG. 1 in the user-initiated "program" mode;

FIG. 36 is an example of the type of information that can be programmed into the watch of FIG. 1;

FIG. 37 is an example of a sample data record from the Administrator System of the present invention;

FIG. 38 is an example of an individual patient record file from the Administrator System of the present invention;

FIG. 39 is an example of the medication data from the individual patient record file of FIG. 38;

FIG. 40 is an example of a sample patient reminder record from the individual patient record file of FIGS. 38 and 39;

FIG. 43 is an example of a sample printed patient compliance report from the Administrative Program of the present invention;

DETAILED DESCRIPTION

Figure 1:
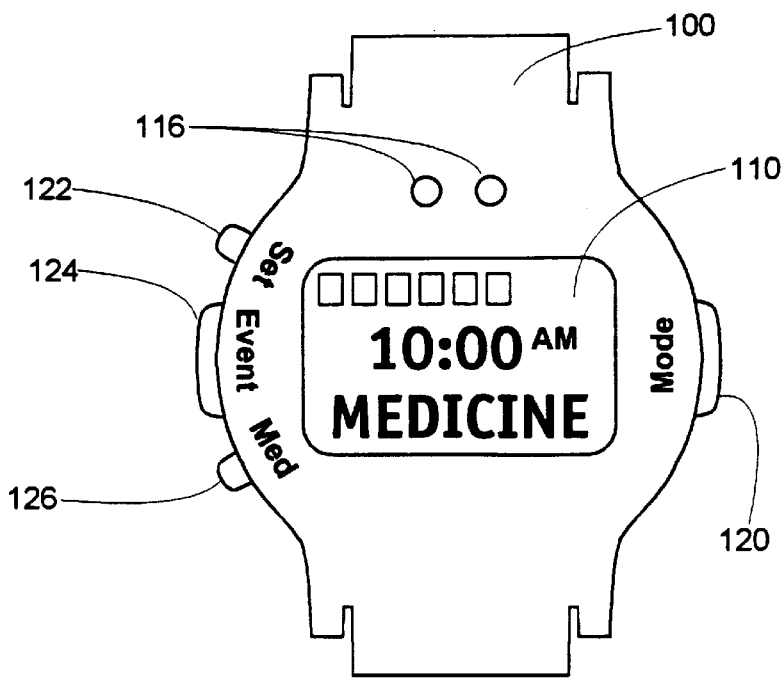
FIG. 1 is an illustration of an embodiment of the electronic watch utilized in a preferred embodiment of the present invention.

The Medical Reminder System provides the end user with programmable electronic, auditory, vibratory, and/or visual reminders for medications to be taken and health care tests or procedures to be performed at very specific times of the day. The device used for this display can also double as a normal electronic LCD watch. The medication schedule, along with other information such as appointment and refill reminders or home health tests to be performed, is downloaded by an infrared link or other communications electronics from the host PC or other external data source or utilization device containing the patient information. The host PC or other data device is intended to be operated by a physician, a pharmacist, some other health care provider or a qualified data entry person, but could possibly be used by the patient if he or she has been properly trained in its operation.

The host system is comprised of a computer with custom software which is incorporated into the health care provider's own patient medication tracking system. Each patient has an individual record which details the patient's name, medical history, medication regimen, prescription history, and scheduled medical tests to be performed. This information is downloaded to the watch through an infrared connection from the PC to the watch or other electronic device. In a preferred embodiment, instructions for multiple specific times for medication reminders or home health tests or procedures can be programmed into the watch. In one embodiment, the system can be operated directly from a standalone PC or pharmacy system.

The watch functions as a data collection device that can be programmed from a host computer system either through a modem or dedicated docking cradle with the ability to upload and download data through infrared detectors and transmitters or other data communications electronics. This data collection device has the ability to generate custom reports of collected information gathered by the device via custom administrative software programs.

The watch is powered by a battery. The electronics include a microprocessor that responds to programming buttons which control the display, the alarm, medical event recording and the downloading and uploading of data through the infrared emitter and detector or other data transfer electronics. A significant feature of the watch is the ability to transmit data through the infrared or other electronic data transfer components. It is through this method of data transfer that the watch is programmed with information from the pharmacist's or health care provider's host system and information can be uploaded back through these sensors to the host system. The electronics include a clock which tracks the time of day, day of the week, and month of the year. The programmable memory stores patient's identification, medications, dosage to be taken, time of day medication is to be taken, medical event history, compliance history, and appointment schedule.

In a preferred embodiment, the invention consists of two main components: the host "Administrative System," resident on a computer or other external data source or data utilization device, and a wristwatch 100 or electronic data collection device, as shown in FIG. 1, having a liquid crystal display (LCD) 110, a piezo alarm buzzer (not shown), an infrared emitter and a detector seen at 116, and four (4) buttons 120, 122, 124, and 126.

The watch has a programmable memory. The watch "normal" mode produces the display illustrated by the example seen in FIG. 5 and provides the user with traditional watch features; time of day 140, day of month 510 and alarm features. The watch is water and shock resistant and its circuitry has a perpetual calendar. The LCD face 110 displays the time in hours and minutes in AM or PM, the number of the day, and the month in a three letter abbreviation.

The watch in its "medication alert mode" records and displays: patient's medical events, medication schedule, medication dosage, name of medication, medication refill reminder, medication taken history, patient compliance success percent, appointment reminder, and name of patient. As seen in FIG. 1, there are four buttons accessible to the user to control the watch operation. These are the MODE 126 and SET 122 buttons and the EVENT 124 and the MED(ication) 120 buttons. The buttons are used for various operations such as indicating the required medication has been taken or to change the time or date. The Watch's piezo buzzer is capable of producing various tones. The frequency of tones available are: 1.2, 1.4, 1.6, 2.0, 2.3, 2.7, 3.3, and 4.1 kHz.

Figure 2:
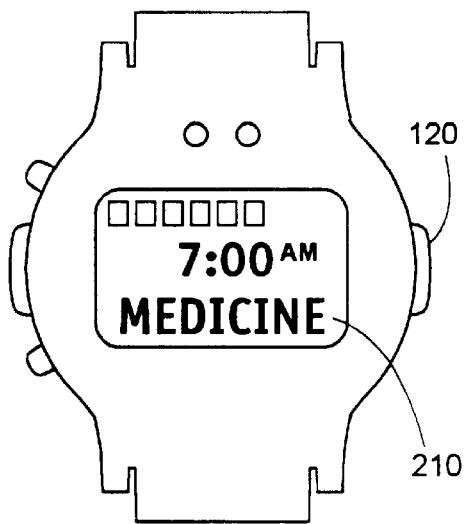
FIG. 2 is a diagram of the watch of FIG. 1 in the "medication alert" mode.
Figure 3:
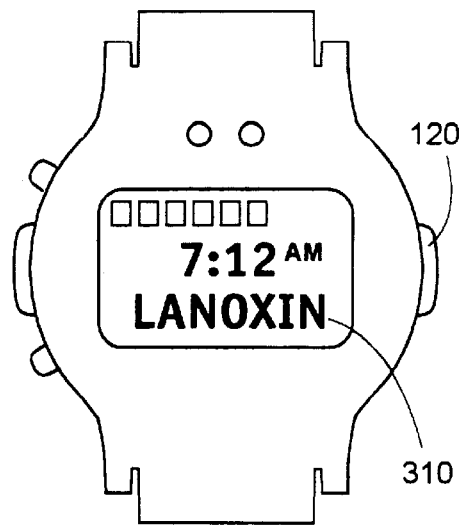
FIG. 3 is a diagram of the watch of FIG. 2, now displaying the name of the medication to be taken at the current time.

The watch "medication alert mode", shown in FIGS. 2 & 3, displays several aspects of the patient's medical regimen on the LCD display 110. The watch functions as a normal watch until the medication alarm is sounded according to the programmed alert function, at which point the watch display flashes the word "MEDICINE" 210, as shown in FIG. 2. The patient acknowledges the alarm by pressing the "MED" button 120 on the side of the watch. As shown in FIG. 3, the name 310 and dosage quantity of the medication to be taken at this time are displayed across the lower portion of the LCD in a special eight character display segment of the LCD. The patient then proceeds to take the medication as indicated on the watch. In a preferred embodiment, up to 16 unique alarm times can be programmed into the watch, each having unique medication information.

Figure 4:
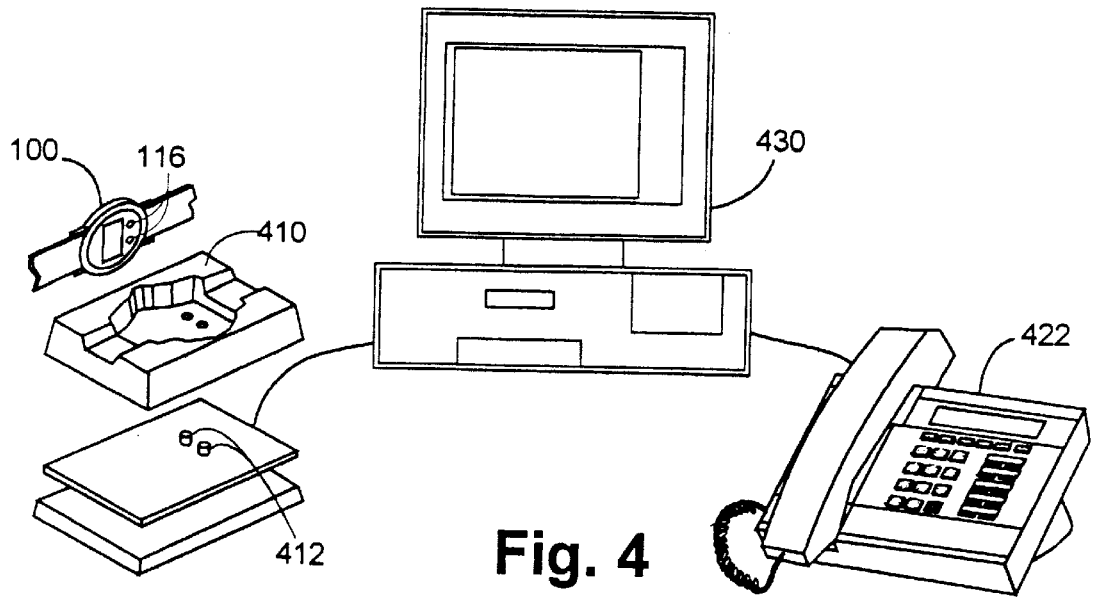
FIG. 4 is a block diagram of an embodiment of the system of the present invention showing the host computer and both a dedicated and a remote docking cradle.

As shown in FIG. 4, in the preferred embodiment of the invention, the medication regimen is loaded into the watch 100 through the infrared detector or other electronic data transfer electronics in the face of the watch by placing the watch in a cradle housing 410 which positions the infrared emitter and detector 116 in the face of the watch 110 in close proximity to the cradle's infrared detector and emitter respectively seen at 412. The infrared devices are connected to electronic circuitry which establishes a serial communication link between a microprocessor within the watch and a personal computer 430. This electronic circuitry may advantageously take the form described in detail in U.S. patent application Ser. No. 08/998,145 filed on Dec. 24, 1997 by R. James Duckworth entitled "Low Power Infrared Communication System."

As illustrated by the connection between the computer 430 and the telephone 422 in FIG. 4, an additional communication link may be established using a modem built into the computer 430 for bidirectionally transferring data between the watch 100 and a remote location via the computer 420 using conventional data communications techniques. The watch 100 can thus be programmed from the either the personal computer system 430 or from a remote computer accessible to a physician or pharmacist to provide programming information to the watch 100 or obtain compliance and status information from the watch 100. If desired, the need for a connected personal computer may be eliminated by including a modem in the cradle housing 412 to establish a serial communication link to a remote location. In this case, the wearer may simply place the watch in the cradle and press a button to establish a dial-up connection with the remote computer, which then identifies the watch by a unique serial number and performs the desired upload and download of information between the watch 100 and the remote computer.

Figure 5:
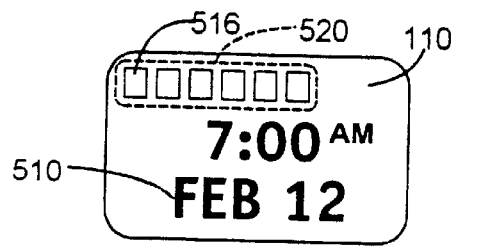
FIG. 5 is a diagram of the display of the watch of FIG. 1 in the "normal operation" mode.

In normal operation, the watch 100 displays the current time 140 and date 510 information, as shown in FIG. 5. The number of medication reminder times for the day is shown by the number of icons 516 displayed on the top line 520. In the preferred embodiment, the watch time 140 is displayed in twelve (12) hour format with the use of the letters AM or PM to indicate if morning or afternoon. Any leading zero on the hours value is suppressed to improve readability. The date information 510 is displayed by showing the month as a 3-character string ("Jan", "Feb", etc.), followed by the day of the month. Any leading zero on the day of the month is suppressed. In the preferred embodiment, the watch changes the current month based on the number of days in the month and automatically adjusts for leap years.

In this normal phase of operation, the watch continuously monitors the time and compares it with the following times: Medication Reminder or Health Test times and Daily Alarm time. If the time matches a stored Medication Reminder or Health Test time, then the watch initiates the Medication Reminder Alarm process. If the time matches the daily alarm time, then the watch initiates the Daily Alarm process.

Figure 6:
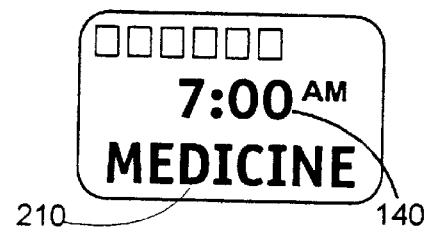
FIG. 6 is a diagram of the display of the watch of FIG. 1 in the "medication alert" mode.
Figure 7:
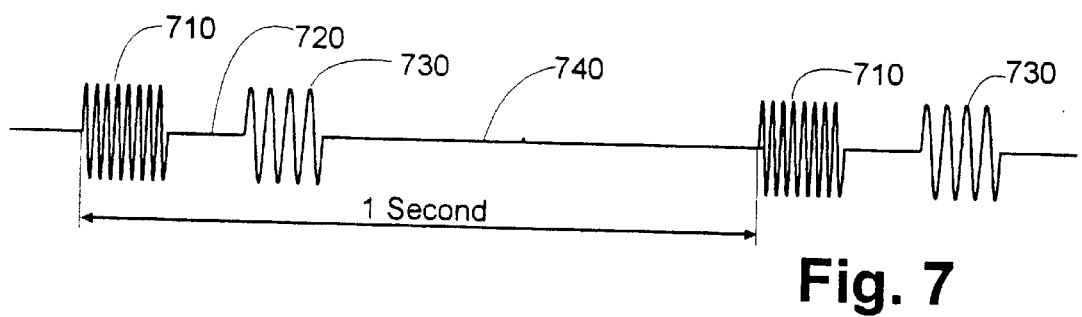
FIG. 7 is a timing diagram of the medication alert beep produced by the watch of FIG. 1.

When the "Medication Reminder Alarm" starts, the watch has to alert the patient. As shown in FIG. 6, the medication icon 610 for the corresponding medication time flashes. The watch also displays the word MEDICINE 210 flashing on the bottom line of the LCD. As shown in FIG. 7, at the same time the watch beeps with the following sequence: a 3.3 kHz tone is sounded for 125 ms 710, followed by 125 ms of silence 720, followed by a 1.6 kHz tone for 125 ms 730. This is then followed by 625 ms of silence 740. This cycle then repeats thirty times, for a total of 30 seconds. In one embodiment, the alarm beep is configured to incrementally increase in volume if the patient does not respond in a specified amount of time. When the alarm sequence has finished, the word MEDICINE 210 continues to flash for a maximum period of 59 minutes. Every 10 minutes, the medication alarm sound of FIG. 7 is repeated. The icon 516 for the next medication reminder time also continues to flash.

As shown in FIG. 8, when the MED button 120 is pressed, the alarm sound ends and the flashing word MEDICINE 210 is replaced with a scrolling message 810 describing the medication to be taken. The message is displayed 7 or 8 characters at a time. When the end of the medication description is reached the message repeats again. For example, as shown in FIG. 9, the display 110 may show the word "LANOXIN" 910 as the message 810 of FIG. 8 is scrolling. The message keeps scrolling and repeating for a maximum period of 59 minutes from the time the medication reminder alarm first sounded.

The medication reminder process is terminated when the patient presses the MED button 120 a second time to indicate that he/she is ready to take the necessary medication. The message stops scrolling and the watch returns to the Normal Phase of operation to display the current time and day information. The watch face has graphic outline boxes at the top line 520 of the LCD 110, corresponding to each medication reminder icon 516. The number of icons 516 correspond to the number of times medications or home health tests should be administered. As shown in FIG. 10, the corresponding "outline" box is filled in by the action of the patient pressing the MED button when the alarm is sounding for a reminder associated with that particular icon 516. The filled-in boxes are a visual record to the patient and aid the patient in tracking the daily scheduled medicine regimen.

The alarm will therefore sound for a maximum of 30 seconds and will shut itself off if the patient presses the MED button 120. The word "MEDICINE" continues to flash across the watch face for 59 minutes or until the MED button 120 is pressed. The audio alarm will continue to repeat every 10 minutes during these 59 minutes. The patient has up until the end of that 59 minutes to acknowledge the message and take the prescribed medication in order to comply with the medication regimen. Finally, as shown in FIG. 10, the medication icon rectangle 1010 is filled in to show that the medication for that period was taken after the patient presses the MED button 120 for the second time.

If the MED button 120 is not pressed twice within the one hour period following the start of the medication reminder alarm, then the medication alarm process ends. The medication reminder message stops scrolling and the alarm stops sounding. It is assumed that the patient did not take the expected medication for this time period, and the medication enunciator rectangle for that particular period is not filled in.

The information that scrolls across the LCD is customized for each patient by the pharmacist; and as a safety factor the patient cannot alter that information by reprogramming of the watch. Programming can only be done when the watch is linked to the pharmacist's or other health care provider's host computer. Other information such as health care tests can also be programmed into the watch. In fact, any custom message can be programmed into the watch by the pharmacist or data entry person.

The watch has an "Advance Operation" that allows the patient to take the medication before the normal time and still have the watch record that the medication has been taken. When the MED button 120 is pressed before a medication alarm is due, the watch assumes that the patient wishes to take the next medication early. As shown in FIGS. 11 and 12, the patient presses the MED button 120, causing the display to flash the message "EARLY?" 1110. The patient again presses the MED button 120 and the "value" EARLY appears on the watch. The patient can press the MED button again if he wants to record that he has taken the medication earlier than prescribed. This allows the patient to keep to a prescribed regimen, but also allows the patient to plan ahead so that the alarm does not sound at an inappropriate time (i.e.; church, library etc.). To stop accidental pressing of the switch from resulting in a false recording, the patient is asked for confirmation by a scrolling message 1120 on the LCD, as shown in FIG. 11. The icon 1210 for the next medication reminder time also flashes, as shown in FIG. 12.

The scrolling message 1120 displays for 60 seconds. If, during this 60 seconds, the patient presses the MED button again, the watch will display the medication 1310 to be taken at this time, as shown in FIG. 13. The watch displays the medication to be taken by scrolling the information as described in the Medication Alarm Process section above. However, unlike the one hour message scrolling period and the ten minute alarm sequence, the medication information is only displayed for ten minutes. During this time, the patient has to press the MED button 120 to record that the medication has been taken at this time.

As shown in FIG. 14, if the patient did take the medication early for a particular time slot (for example, at 10:30 instead of at the normal time of 11:00), then the medication graphic 1410 for the 11:00 time period is filled in and the medication alarm process is canceled for 11:00. The watch returns to "normal" operation mode, displaying the date 510 and time 140.

The watch also has a "Medication Alarm Process Defer Option", which allows the patient defer taking the medication for one hour after the start of the medication reminder alarm. The defer operation is executed in the same way the medication reminder alarm is executed. This allows the patient to take medication up to one hour after the start of a medication reminder alarm and still have the watch record the compliance.

A "Refill Reminder" can also be programmed into the watch. This feature reminds the patient to return to the pharmacy for a refill of a prescription. The watch displays this information when a normal medication alarm cycle ends. While the medication reminder alarm is in process (medication message scrolls and the alarm sounds) the patient presses the MED button 120 to indicate the medication for that time has been taken. Normally the watch would return to the time and date display. However, if there is a refill reminder or an appointment pending, then the watch immediately displays the new information while also sounding an alarm for 10 seconds.

As shown in FIG. 15, the word "REFILL" 1510 appears on the LCD after the medication reminder alarm has sounded and the patient has pressed the MED button 120 twice. The patient then presses the MED button again, and the message 1610 about which medication to refill scrolls across the watch screen, as shown in FIG. 16. This refill reminder is preferably set to alert the patient several days before the medication runs out. The scrolling reminder message ends if the MED button is pressed again or after a time-out interval of 2 minutes. When it is time to refill the prescription, an "Rx" (Pharmacy icon) symbol 1710 at the top of the display also flashes, as shown in FIG. 17. The "Rx" symbol 1710 is preferably displayed starting several days before the prescription runs out and continues to be displayed until the watch is returned to the pharmacy and reprogrammed.

Appointments can also be programmed into the watch, and are responded to in the same manner as refill reminders. The word "APPTMNT" appears across the LCD after the alarm has sounded and the patient has pressed the MED button. The appointment message scrolls across the watch screen after the medicine regimen is displayed. The appointment reminders are displayed a number of days before the appointment and on the day of the appointment. They are canceled after the day of the appointment. They are displayed on the watch LCD in a manner similar to the refill reminders, discussed in conjunction with FIGS. 16 and 17.

The watch also has a "Daily Alarm" feature. When the watch time matches the daily alarm time (assuming the alarm was set), then the Daily Alarm process initiates to alert the patient. As shown in FIG. 18, a bell icon 1810 flashes on the LCD 110. At the same time, the watch beeps for a maximum of 30 seconds, as shown by the timing diagram of FIG. 19. The Daily Alarm will end after 30 seconds and the watch will return to the Normal Phase of operation and display the current time and day information. The alarm will also end if any button is pressed.

The watch has several modes of user-initiated operation, which it looks for by continuously monitoring the state of the four buttons. The watch mode may be changed by the user at any time by pressing the MODE button 126. The different modes are: Set Time/Day; Set Alarm; Review Medication Schedule; Review History; Review Events; and Program.

The different modes of user-initiated operation are pictured in FIGS. 20 to 35. The Set Time mode is selected by pressing the SET button 122, causing "SET TIME" 2010 to be displayed on the LCD 110. The watch then starts the minutes part 2110 of the time display 140 flashing, as shown in FIG. 21. The minutes 2110 can now be changed by pressing the SET button 122. Each time the SET button 122 is pressed, the minutes increment by one. Holding down the SET button 122 causes the minutes value to scroll at the rate of 2 per second.

To change the hours, the MODE button 126 is pressed. This causes the hours value to flash. Pressing the SET button 122 changes the hours value. If the hours value goes past 12 then the AM/PM indicator changes. To change the day, the MODE button 126 is pressed. This causes the day value to flash. Pressing the SET button 122 changes the day value. The month is also set in a similar manner. The Set Time mode is ended by pressing the MODE button 126 while the month value is flashing. The time is now set. The Set Time mode is also automatically ended if no button is pressed for a period of 20 seconds. After ending the Set Time Mode, the watch enters the normal Display Time/Date phase.

Pressing the SET button 122 then causes the Set Alarm mode to be started, as shown by the words "SET ALARM" 2210 displayed on the LCD 110 in FIG. 22. As shown in FIG. 23, the display changes to "ALM TIME" 2310. The minutes value flashes. Pressing the SET button 122 causes the minutes value to increment. Pressing the MODE button 126 allows the hours value 2410 to be changed, as shown in FIG. 24. Pressing the MODE button again allows the Alarm to be turned on or off. If the alarm is currently enabled, the bell symbol 2510 is illuminated, but not flashing, as shown in FIG. 25. Pressing the SET button 122 toggles the alarm on or off, as shown by the bell symbol being turned on and off. Pressing the MODE button 126 sets the Alarm if it was enabled (indicated by the alarm bell icon). The display then reverts back to the normal time and date display.

The "Review Medication Schedule" mode is selected by pressing the MODE button 126 until the "Schedule Mode" is entered, shown in FIG. 26 by the display of the word "SCHEDULE" 2610 on the LCD 110. In this mode the display scrolls to show the patient name, contact information, and medication regimen on the message line 2710, as shown in FIGS. 27 and 28. The name scrolls across the line seven (7) or eight (8) characters at a time from right to left. This feature identifies the owner of the watch and allows contact information to be available when the patient is unable to give it. Pressing the SET button 126 again allows the time of the first medication and the name and quantity of medications to be taken to be displayed, as shown in FIG. 29.

The description of the medication (e.g. CAPOTEN 25 MG/LASIX 40 MG/LANOXIN 0.125 MG) is displayed on the message line 2910. The description scrolls across the line. While the prescription information is scrolling, the medication rectangle icon 2920 for that particular time also flashes. Pressing the SET button 122 again allows the time of the second medication and name and quantity of medications be taken to be displayed. The SET button is pressed to display each additional time at which medications are required. The Review Medication Mode is ended by pressing the MODE button 126. The watch then displays the normal time and date information.

A record of patient compliance for each of the medication reminders is stored in the watch. This information may be displayed by using the Review History Mode or by uploading the compliance data to the Pharmacy computer system. The watch Review History mode is accessed by pressing the MODE button 126, causing the word "HISTORY" 3010 to be displayed on the LCD 110, as shown in FIG. 30A. The LCD display sequences through the activity that was recorded on the watch. The patient thus has a visual record of his or her compliance success rate. The days and times that the patient was not compliant is displayed 3020 by showing the graphic box display 3022 for each day when there was noncompliance, as seen in FIG. 30B.

The watch also calculates the number of times that medications were scheduled to be taken and displays the compliance success rate of the patient in both actual numbers 3110 and a percentage 3112, as shown in FIGS. 31 and 32. Pressing the SET button 122 again allows this compliance information to be displayed on the LCD 110, as shown in FIG. 32. The watch displays the history of the medication taken. For each day the medication icons are turned on to indicate if the patient pressed the MED button 120 while the medication alarm was active. For example, FIG. 30B shows that on this time and date the patient had missed the third medication period for that day. In the preferred embodiment, the watch has two modes of history review: 1) Only the days are displayed for which the patient did not take all the required medication, and 2) All history days are displayed.

The watch has a feature for recording medical events. The patient records the medical event by pressing the EVENT button 124 on the side of the watch. The watch records the action and date stamps the event record. This medical event record can be retrieved by either the patient or the doctor. The events are retrieved by pressing the MODE button 126 until the word "EVENTS" 3310 is displayed on the watch face, as shown in FIG. 33A, and then pressing the SET button 122 to activate the event history that is stored in the watch. The Event Mode will then show the number of events that have occurred since the watch was last programmed. For example, the display in FIG. 33B indicates that 25 events 3320 have taken place. The watch will display the last 20 events and the time when each event was recorded by the watch user. Pressing the SET button 122 again allows the last 20 event information to be displayed. For example, in FIGS. 34A and B, the display 110 shows that on FEB 19 the patient pressed the EVENT button 124 twice.

In order to simplify the history review, only the last 20 events are displayed. Pressing the SET button 122 again returns to the Normal time and day display. If there no events have occurred, or this function was not enabled by the programmer, then the screen of FIG. 33A does not display.

The watch has the ability to download information from the pharmacist's or health care provider's computer, as well as to upload the data stored in the watch to the pharmacist or managed care provider. This transfer of information is done through an infrared transmitter and receiver or other electronic data transfer method, preferably located on the face of the watch. As previously discussed, in the preferred embodiment, the watch is placed into a dedicated holder (e.g. a cradle docking station) which is wired into the host computer. This cradle docking station can alternatively be linked to the host computer via a modem that is an integral part of the cradle device.

The programming of the medication regimen into the watch is accomplished by use of the cradle which is interfaced to the host computer system. The watch nests into the dedicated cradle so that the infrared sensors or other communication links on the watch are aligned to the sensors in the cradle. Through these sensors, information is downloaded into the watch from the pharmacist's or health care provider's computer and the information in the watch is uploaded through these infrared sensors back to the computer. The patient's compliance history stored in the watch is recorded into patient's file on the host computer.

The "Program Mode" is used by the Pharmacist or health care provider or other data entry person and allows the watch to communicate with the pharmacy computer system or any other designated PC host system. As shown in FIG. 35A, the word "PROGRAM" 3510 is shown on the display 110 when the Program mode has been entered. Similarly, when the watch is placed in the cradle, the word "CRADLE" 3520 is displayed, as shown in FIG. 35B. An example of the type of information that can be input into the watch is shown in FIG. 36.

The Administrative Program that is loaded onto the host computer can produce detailed formatted reports from the data that is uploaded to the computer from the watch through infrared transmitter and receiver links or other electronic data transfer method. Graphic records can also be produced as a result of these reports. This documentation greatly aids the patient to better understand the results of his or her compliance efforts for their medicine regimen.

Figures 37, 38:
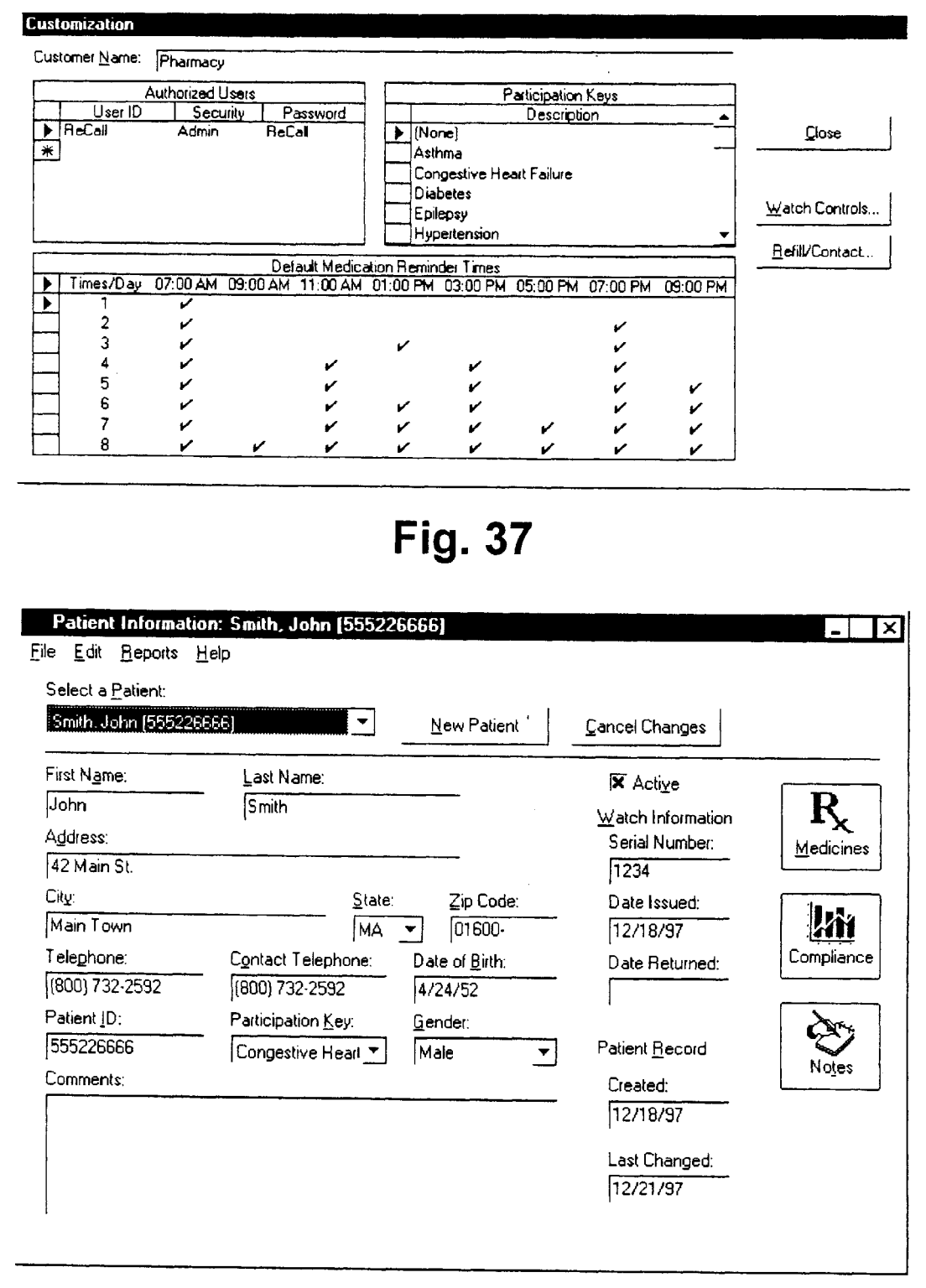

The Administrative Program or System is software that is loaded by the pharmacist or data entry person onto a PC or host computer system. This software manages the information of the Medication Reminder system and interfaces its key data fields with the pharmacist's drug prescription system. A sample data record window is shown in FIG. 37. This information is segmented into files pertaining to individual patients. A separate file is kept for each individual, as seen in the example shown in FIG. 38. The files contain such information as the patient's name, Social Security number, address, telephone number, Medicare number, types of medication, medication history, refill schedule, compliance history, appointment schedule, doctor(s) and, if pertinent, the patients managed care organization and other custom information. The medication type, dosage amount and frequency is entered into the patient's record as shown in FIG. 39. Other patient reminders such as performing a health care test or procedure or recording a doctor's appointment can also be added to the patient's record (FIG. 40).

Figure 41:
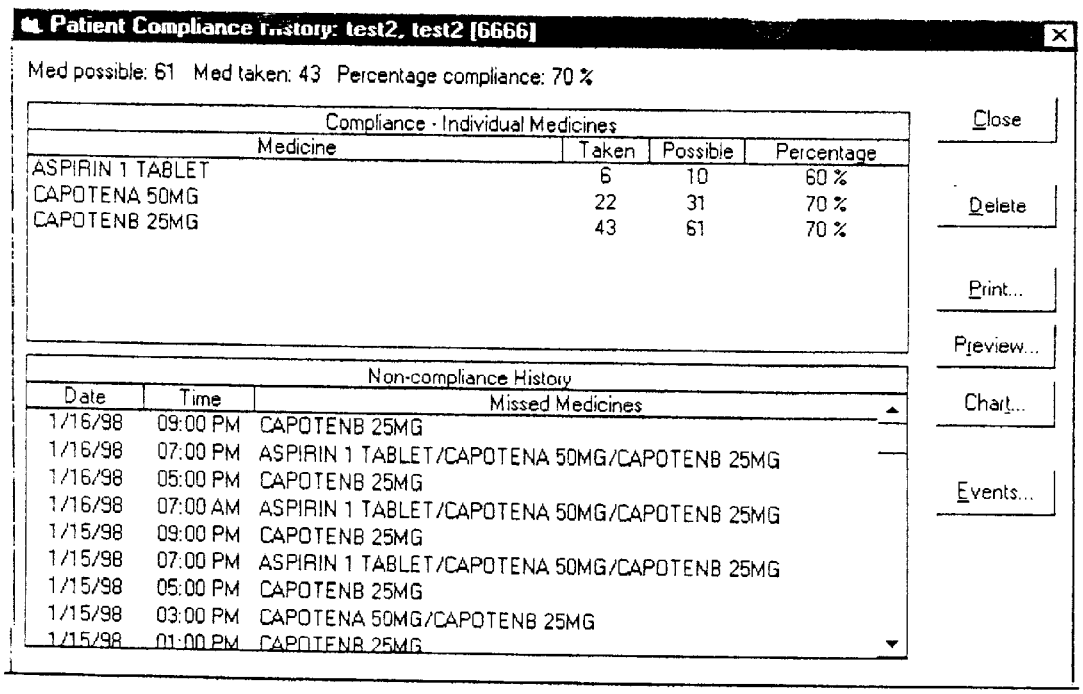
FIG. 41 is an example of a sample patient medication compliance and event record from the Administrative Program of the present invention.
Figure 42:
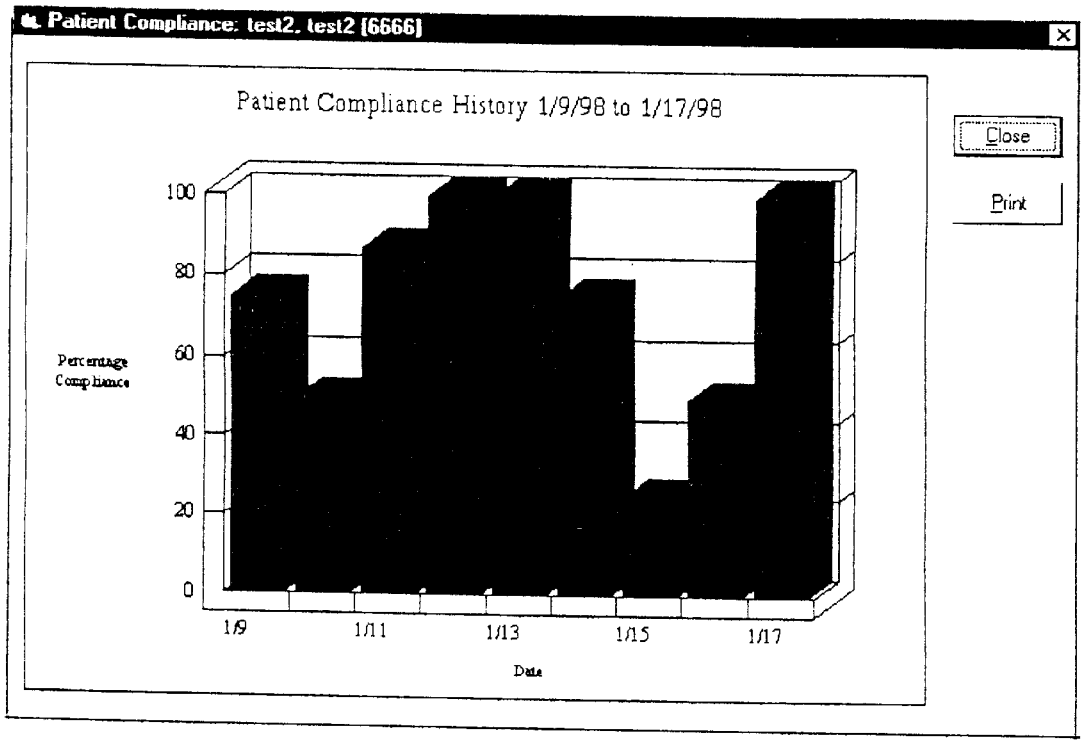
FIG. 42 is an example of a sample patient compliance graph from the Administrative Program of the present invention.

The Administrative System software is then used by the pharmacist or data entry person to program information into the watch for each patient. This system consists of several screens with information pertinent to the patient. These screens can be customized for individual patients. A detailed compliance record can also be retrieved and displayed for each patient, as shown in FIGS. 41 and 42. New patients can be added into the system at any time. A printed report with each patient's information can also be obtained from the system, as shown in FIG. 43.

In one embodiment of the system, the watch is designed to be programmed and used as a system to lead the patient through a series of questions and then collect the patient's responses. The watch may also prompt the patient for specific information at set times of the day. For example, the patient may be prompted to enter his or her blood pressure reading, or to respond to other questions by selecting from a set of alternative choices. This embodiment of the watch allows multiple events to be recorded, e.g. that the patient is experiencing shortness of breath, chest pain, and dizziness. The name and description of events that may be recorded may be programmed into the watch on a patient-by-patient basis using the Administrative software.

In this embodiment of the watch, a Patient Query message causes the watch to beep like a daily medication reminder alarm at the pre-programmed time. There are normally two types of Patient Query messages. The first type requires the patient to provide a numerical response to the query, e.g. a blood pressure or temperature reading. The second type requires the user to select a response from a set of choices; for example, in response to the query "How do you feel?" the user may select from among "very well", "OK", "not good" or "ill." Either type of query can be prompted by any specific date/time, or as a result of pressing one of the multiple medical event buttons.

Figure 44:
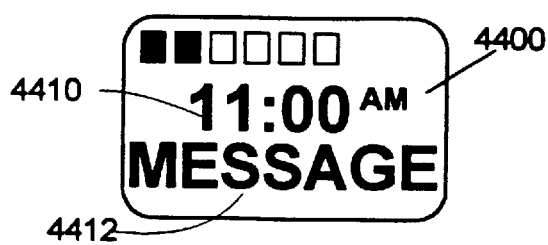
FIG. 44 is a diagram of the display of the watch of FIG. 1 in the "patient query" mode.

As shown in FIG. 44 for this embodiment, for each type of query the watch will beep and the watch display 4400 will display the time 4410 and the word "MESSAGE" 4412. When the MED button 120 is pressed, the alarm sound ends and the flashing "MESSAGE" 4412 is replaced with a scrolling message that contains either a query or an action to be carried out, for example, "TAKE BLOOD PRESSURE AND PRESS MED BUTTON". When the patient has taken his or her blood pressure, he or she presses the MED button 120 a second time to indicate that the information is ready to be recorded.

Figure 45:
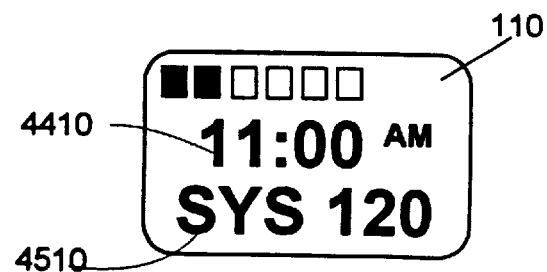
FIG. 45 is a diagram of the display of the watch of FIG. 44, prepared to receive the first patient numerical response.

For this example, the patient enters the systolic and diastolic pressure readings. The watch first prompts for the systolic pressure, e.g. "ENTER SYSTOLIC PRESSURE." The patient then presses the MED button again, changing the watch display to a flashing default value 4510 as seen in FIG. 45. The patient presses the SET button 122 to increase the value, or uses the MODE button 126 to decrease the value, until the value representing the measured systolic pressure is reached. The button may be held down to increase the rate of scrolling. Once the correct value has been reached, the patient presses the MED button 120 again to record the value.

Figure 46:
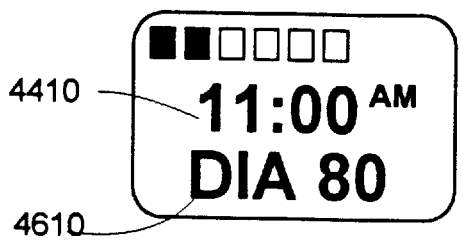
FIG. 46 is a diagram of the display of the watch of FIG. 44, prepared to receive a second patient numerical response.

For this example, the watch then prompts for the entry of the diastolic pressure, e.g. "ENTER DIASTOLIC PRESSURE". The patient presses the MED button again and the display changes to a flashing default value 4610, as shown in FIG. 46. Using the SET and/or MODE buttons, the patient modifies this default value until the measured diastolic pressure is displayed. Once the correct value is displayed, the patient presses the MED button to record the value. The watch then returns to the normal date and time mode, as shown in FIG. 5. While the preceding example illustrates how a patient can provide two numerical responses to a query, it is clear that other queries requiring one or multiple responses from the patient may be utilized and responded to in the same manner, requiring a corresponding fewer or greater number of steps.

Figure 47:
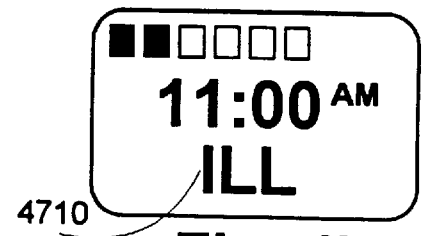
FIG. 47 is a diagram of the display of the watch of FIG. 44, prepared to receive a patient response chosen from among a preset selection of responses.

In one embodiment, the watch provides a set of alternative responses from which the patient may select in response to a query, rather than entering a numerical value as in the previous example. In this embodiment, when the MED button 120 is pressed, the alarm sound ends and the flashing word "MESSAGE" 4412 of FIG. 4 is replaced with a scrolling message posing a question, e.g. "HOW DO YOU FEEL?". When the patient presses the MODE button 126 a set of alternative scrolling responses are displayed, e.g. "VERY WELL", "OK", "POOR", "ILL", with a new one being displayed each time the MODE button is pressed. After all possible responses have been displayed, the next push of the MODE button will repeat the question, after which the patient may again cycle through the possible responses. As seen in FIG. 47, the patient selects a particular response 4710 by pressing the MED button while that response is displayed.

Figure 48A:
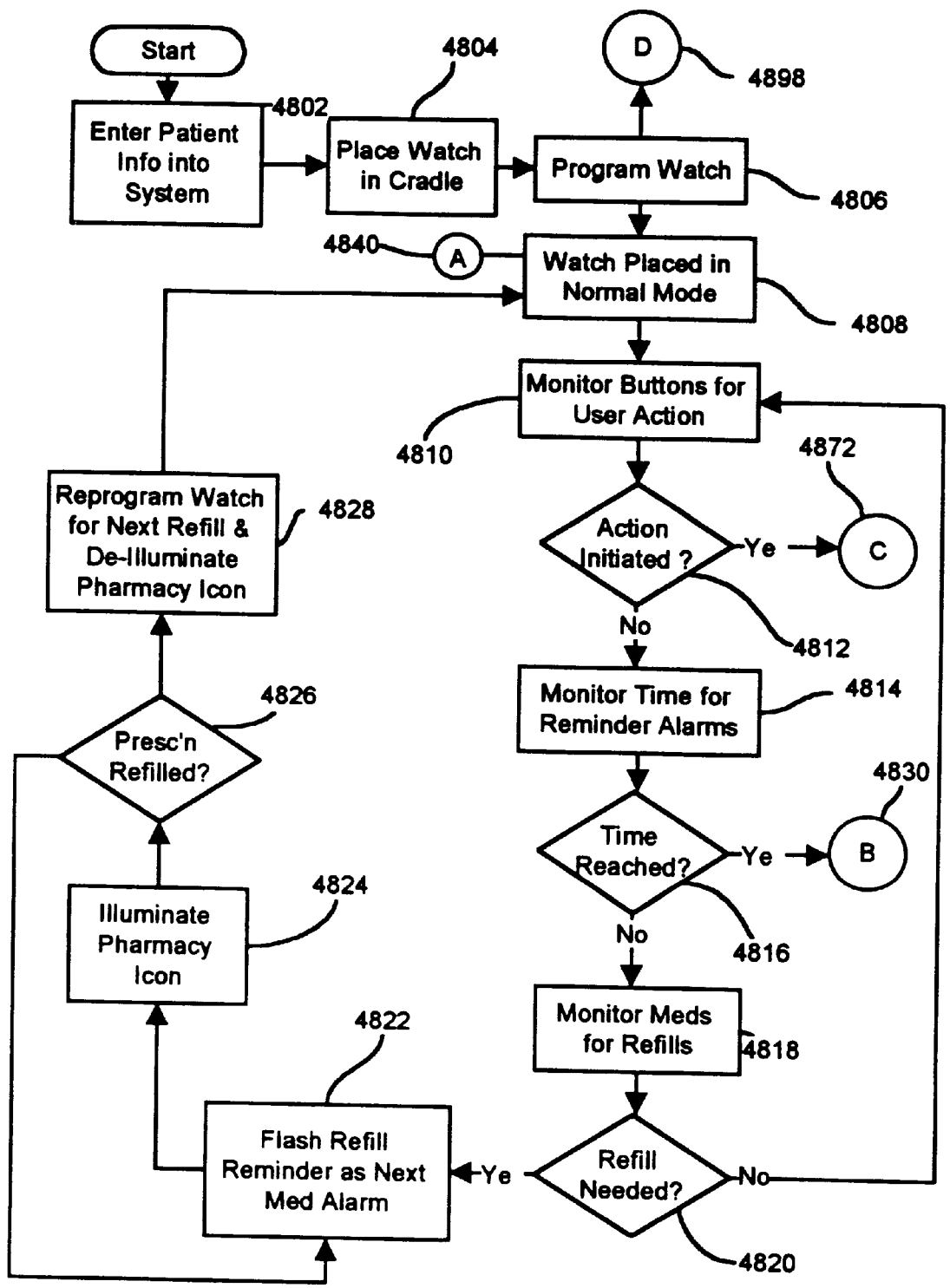
FIG. 48A, B and C together are a block diagram illustrating the basic operation of a particular embodiment of a system constructed according to the present invention.
Figure 48B:
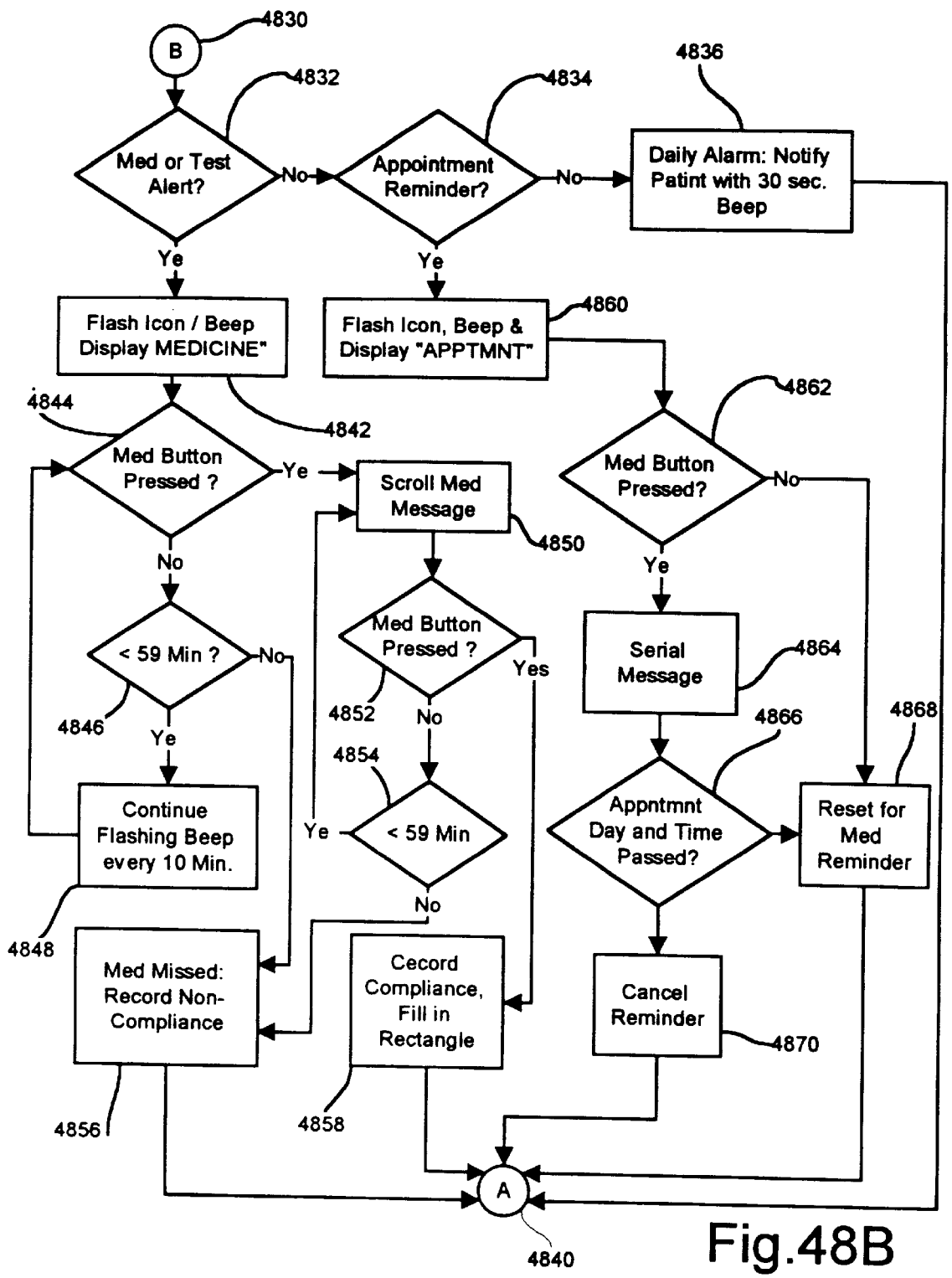
Figure 48C:
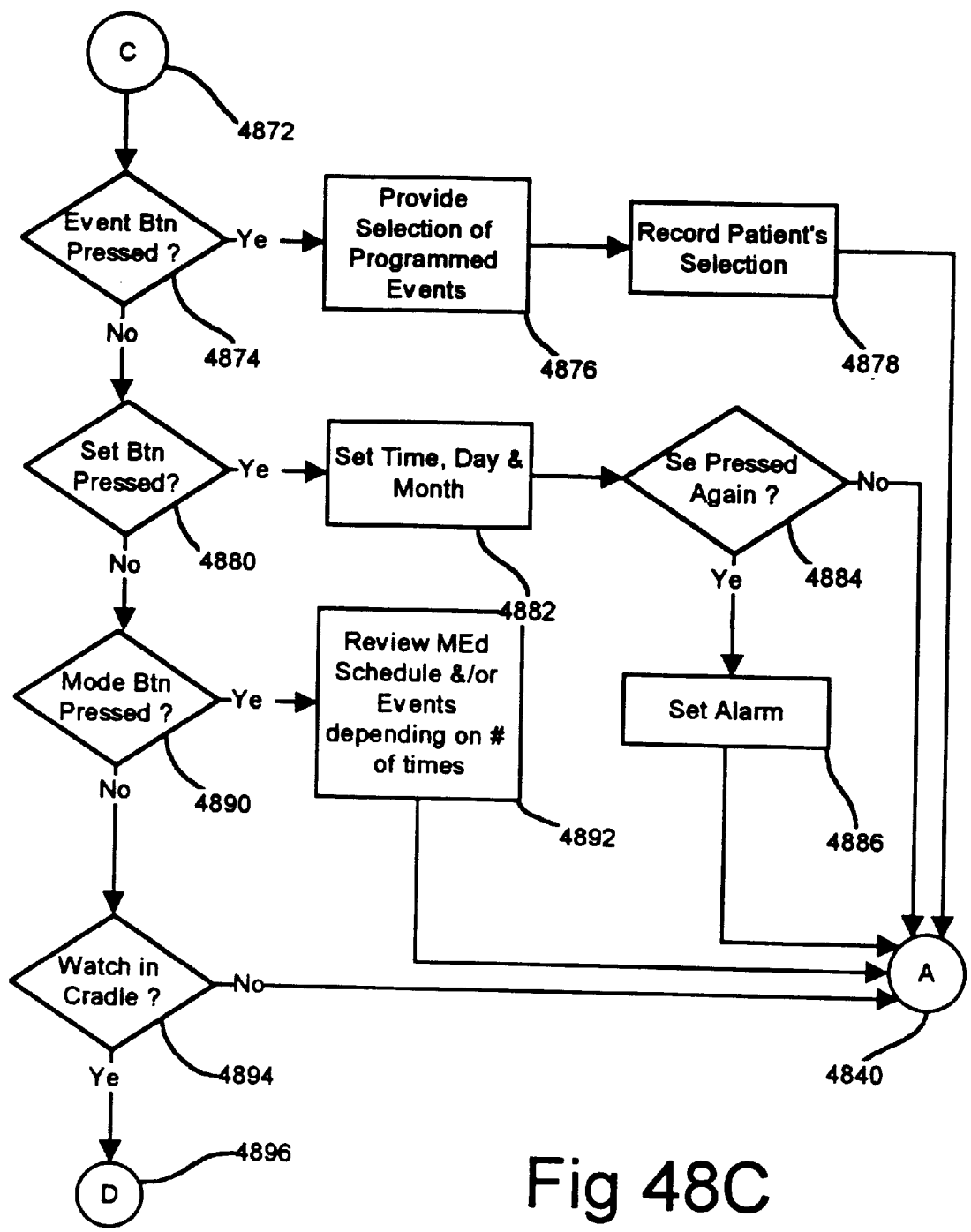

A block diagram illustrating the operation of a basic embodiment of the invention is shown in FIGS. 48A–C. As shown in FIG. 48A, the patient information is entered into the host computer system 4802 by the pharmacist or other health care provider. The watch is placed into the cradle 4804 and programmed 4806 with the reminder times and other commands. After programming 4806, the watch enters the normal operation mode 4808. The four watch buttons are constantly monitored for user-activated events 4810. If such an event is initiated 4812 by the user pressing one of the watch buttons, the watch enters the user-initiated operation mode 4872.

If no user-initiated event occurs, the watch remains in normal mode, continues to monitor the buttons, and also monitors the time for reminder alarms 4814. If a preset alarm time arrives 4816, the watch enters the medication alert mode 4830. If it is not currently a preset alarm time, the watch continues to monitor the buttons and time, and also monitors the medication schedule for programmed refill alerts 4818. If it is not time for a refill 4820, the watch remains in normal mode, monitoring the buttons, medication times, and refill schedule.

If it is time for a refill of a particular medication 4820, at the next medication alert event the refill reminder is flashed 4822 and the pharmacy icon is illuminated 4824. This will continue to occur until the prescription has been refilled 4826 and the watch reprogrammed with the date of the next refill 4828. Once the watch has been reprogrammed 4828, it returns to the normal mode of operation 4808 until the next user-initiated action or alert event occurs.

As seen in FIG. 48B, when the watch is in medication alert mode 4830, the type of alert affects the next action to be taken, f the alert is neither a medication or health care test/procedure alert 4832 or an appointment reminder 4834, it is assumed to be a daily alarm 4836. The patient is notified by a 30 second maximum beep, which may be halted earlier by the patient pressing a button. After the daily alarm is given 4836, the watch returns to normal operation mode 4840.

If the alert is a medication or health care test/procedure alert 4832, the watch flashes the relevant icon, produces the alert beep and displays the word "MEDICINE" 4842. When the patient presses the MED button 4844, the medication or health care test/procedure message is scrolled 4850. Otherwise, the watch continues to flash the icon and beep every 10 minutes 4848 for a total of 59 more minutes 4846. Once the additional 59 minutes have passed 4846, the watch assumes that the medication dose was missed and records a noncompliance event 4856, after which it returns to normal operation 4840.

Once the medication message is scrolling 4850, the patient has another 59 minutes to take the proper medication and press the MED button 4852 to indicate compliance. The message will continue to scroll 4850 for a further 59 minutes 4854 unless the MED button is pressed 4852. After the 59 minutes has passed 4854, the watch assumes that the medi-cation dose was missed and records a noncompliance event 4856, after which it returns to normal operation 4840. If the MED button is pressed by the patient to indicate compliance 4852, the watch records compliance and fills in the associated rectangular graphic outline box 4858, after which it returns to normal mode 4840.

If the alert is an appointment reminder 4834, at the next medication alert the relevant icon is flashed, a beep is sounded, and the LCD displays the word "APPTMNT" 4860. If the MED button is subsequently depressed 4862, the appointment reminder message is scrolled on the LCD 4864. Once the appointment date and time have passed 4866, the reminder is canceled 4870 and the watch returns to normal operation mode 4840. Even if the patient does not press the MED button 4862, if the appointment day and time has not passed 4866, the watch will reset the reminder function to be ready for the next medication alert 4868, after which it returns to normal operation mode 4840.

As seen in FIG. 48C, in user-initiated operation mode 4872, the watch first determines which button has been pressed. If the EVENT button has been pressed 4874, the patient is presented with a scrolling list of medical events that have been programmed into the watch for that patient 4872. The patient selects the event from the options on the list that describes the event being experienced, and the selection is recorded in the watch 4878 for later transfer to the host computer. The watch then returns to normal operation mode 4840.

If the SET button has been pressed 4880, the patient may set the time, day, and/or month 4882, using a combination of the SET and MODE buttons. Then, if the SET button is pressed again 4884 while in the "SET MONTH" function, the watch allows the patient to set the alarm 4886. If the SET button is not pressed again 4884, or if the patient abandons the set time/date task, the watch will timeout after 20 seconds and return to normal operation 4840, just as it does after the alarm is set 4886.

If the MODE button has been pressed 4890, the watch provides a review of the patient's medication schedule, a review of the patient's recent compliance history, and/or a review of the recently recorded events 4892, depending on the number of times the MODE button has been pressed. After all desired data reviews have been completed, the watch returns to normal operation 4840.

If the watch has been placed in the cradle 4894, it enters the program mode 4898, during which it is programmed by the host computer 4806 and uploads event and compliance information to the computer. Once all information has been exchanged between the host computer and the watch in program mode 4898, the watch is removed from the cradle and enters the normal mode of operation 4840.

It is understood that the specific mechanisms and techniques described are merely illustrative of some of the applications of the principles of the invention. Modifications and substitutions by one of ordinary skill in the art of the methods and apparatus described are considered to be within the spirit and scope of the present invention, which is not to be limited except by the claims which follow.

What is claimed is:

1. A reminder system comprising, in combination, an electronic wristwatch including:

timing means for indicating the current date and time, a memory for storing a plurality of programmed messages each consisting of displayable message text and an associated date and time value indicating when said message text should be communicated to the wearer of said wristwatch, a display for visually presenting said message text the wearer of said wristwatch, an audible alarm device, means for comparing said current date and time indicated by said timing device with the date and time value in said messages to actuating said audible alarm device when a given one of said messages should be communicated to the wearer, input means operable by the wearer of said wristwatch for deactivating said alarm device to acknowledge said given one of said messages, an event memory for storing event data including the date and time when said input means is activated by the wearer, and a bidirectional communications port for receiving downloaded data including said messages from an external source and for transmitting uploaded data including said event data to an external device, and a external host computer coupled by a bidirectional communications pathway to said communications port in said wristwatch, said host computer comprising:

means for accepting from a user the message text and a date and time for each message of a set of messages, means coupled to said bidirectional pathway for transmitting said set of messages as downloaded data to the communications port of said electronic wristwatch for storage therein, means coupled to said bidirectional pathway for receiving uploaded data including said event data via said pathway from said electronic wristwatch, and output means for producing an event report derived from said event data.

2. A reminder system as set forth in claim 1 wherein the message text of at least a first one of said messages specifies a procedure to be performed at the date and time specified by said first message.

3. A reminder system as set forth in claim 3 wherein said procedure to be performed is the administration of an medication identified in the message text of said firs of said messages.

4. A reminder system as set forth in claim 1 further includes means responsive to the deactivation of said alarm for initiating the display of the message text of said given one of said messages, means responsive to a further actuation of said input means for terminating the display of said message text of said given message, and means for storing the date and time of said further actuation in said event memory.

5. A reminder system as set forth in claim 1 wherein said display in said wristwatch displays variable length text messages in a scrolling motion such that message text having more characters than the capacity of said display can be viewed in a timed sequence by the wearer.

6. A reminder system as set forth in claim 1 wherein at least one of said messages includes a request for information from the user and wherein said input means operable by said wearer accepts a response to said request which is recorded as event data which is thereafter transmitted via said pathway to said host computer.

7. A reminder system as set forth in claim 1 wherein said bidirectional port in said wristwatch comprises an infrared emitter and detector and wherein said pathway includes an adapter which houses a corresponding infrared detector and emitter to form a bidirectional infrared communications link.

8. A reminder system as set forth in claim 1 wherein at least some of said messages specify a plurality of event times and wherein said display includes means for displaying an plurality of zones corresponding to said plurality of event times with a symbol being displayed in each such zone which indicates the nature of the wearer's response at each of corresponding event time.

* * * * *